United States Patent [19]
Mallette

[11] Patent Number: 5,284,158
[45] Date of Patent: Feb. 8, 1994

[54] SENSITIVE CONDOM

[76] Inventor: Kermit J. Mallette, 3923 South Dakota Ave. NE., Washington, D.C. 20018-3037

[21] Appl. No.: 867,870

[22] Filed: Apr. 13, 1992

[51] Int. Cl.$^5$ .............................................. A61F 6/04
[52] U.S. Cl. ..................................... 128/844; 128/918
[58] Field of Search ................... 128/842, 844, 918; 604/330, 347-353

[56] References Cited

U.S. PATENT DOCUMENTS

| | | |
|---|---|---|
| Re. 33,206 | 5/1990 | Conway . |
| 2,410,460 | 11/1946 | Robinson ........................ 128/844 |
| 4,232,675 | 11/1980 | Meldahl . |
| 4,320,752 | 3/1982 | Comparetto . |
| 4,475,910 | 10/1984 | Conway . |
| 4,638,790 | 1/1987 | Conway . |
| 4,795,425 | 1/1989 | Pugh ............................. 128/844 |
| 4,821,742 | 4/1989 | Phelps . |
| 4,840,188 | 6/1989 | Heidenfelder ................. 128/844 |
| 4,972,849 | 11/1990 | Park ............................. 128/844 |
| 4,984,582 | 1/1991 | Romaniszyn . |
| 5,017,625 | 5/1991 | Ansell . |
| 5,027,831 | 7/1991 | Reddy . |
| 5,036,863 | 8/1991 | Wheeler ........................ 128/844 |
| 5,070,890 | 12/1991 | Papurt . |
| 5,082,004 | 1/1992 | Reddy ........................... 128/844 |
| 5,102,405 | 4/1992 | Conway ......................... 128/844 |
| 5,163,448 | 11/1992 | Foldesy ......................... 128/844 |

Primary Examiner—Michael A. Brown
Attorney, Agent, or Firm—Cushman, Darby & Cushman

[57] ABSTRACT

An improved condom for human sexual intercourse for improved sensitivity, prevention of pregnancy as well as for providing an effective barrier against transmittal of certain diseases such as spread of HIV for AIDS, gonorrhea, non-specific urethritis, male urinary tract diseases as well as female pregnancy related diseases. The sensitive condom comprises a membrane condom which is reinforced at the head of the penis by latex rubber or polyurethane which prevents osmotic transmission of bodily fluids. A generic spermicide such as nonoxynol 9 is also added at the front end of the condom to deactivate HIV. The packaging includes braille markings for orientation such that it can be donned properly even in the dark.

9 Claims, 1 Drawing Sheet

SENSITIVE CONDOM

This invention relates to an improvement in condom construction and design for increased sensitivity during human sexual intercourse as well as for prevention of certain sexual diseases of the male and the female sex organs.

A prior art search was conducted and the following U.S. Patent documents were uncovered arranged in reverse a chronological order.

a) U.S. Pat. No. 5,070,890 granted to David Papurt on Dec. 10, 1991 for, "Male Condom Device and Method of Using Same"
b) U.S. Pat. No. 5,027,831 granted to A. V. K. Reddy on Jul. 2, 1991 for, "Prophylactic with Glans Penis Stimulation"
c) U.S. Pat. No. 5,017,625 granted to Christopher Ansell on May 21, 1991 for, "Adhesive Their Preparation & Use Polyurethane Containing Acrylate Group"
d) U.S. Pat. No. 4,984,582 granted to Gregory & Eva Romaniszyn for, "Vacuum Assisted Condom Applicator"
e) U.S. Reissue Patent No. 33206 granted to James, Peter & Phillip Conway for, "Male Condom Catheter having adhesive on Rolled Portion". (Reissue of H infra)
f) U.S. Pat. No. 4,821,742 granted to John Phelps III on Apr. 18, 1989 for, "Contraceptive Device".
g) U.S. Pat. No. 4,638,790 granted to James Peter & Phillip Conway on Jan. 27, 1987 for, "Contraceptive Hood"
h) U.S. Pat. No. 4,475,910 granted to James Peter & Phillip Conway on Oct. 9, 1984 for, "Male Condom Catheter Having Adhesive on Rolled Portion". (Reissued at E supra)
i) U.S. Pat. No. 4,320,752 granted to John Comparetto on Mar. 23, 1982 for, "Multiband or Network Male Contraceptive"
j) U.S. Pat. No. 4,232,675 granted to Edward Meldahl on Nov. 11, 1980 for "Male Contraceptive Arrangement".

Unfortunately prior art condom devices do not meet all of the following objectives established by the inventor for this invention.

OBJECTIVES

1. It is an objective of this invention that the condom provide increased sensitivity during human sexual intercourse and more particularly during orgasm.
2. Another objective of this invention is that it prevent the spread of HIV virus which in turn will prevent the spread of AIDS.
3. Another objective of this invention is that it prevent the spread of gonorrhea.
4. Another objective of this invention is that it prevent the spread of nonspecific urethritis.
5. Another objective of this invention is that it prevent the spread of male urinary tract diseases.
6. Another objective of this invention is that it prevent pregnancy in females.
7. Another objective of this invention is that it prevent the spread of female pregnancy related diseases.
8. Another object of this invention is to provide a means for preventing the drying of the membrane.
9. Another objective of this invention is to provide a means for protection of certain pathogens.
10. Another objective of this invention is that it be packaged in a hermetically sealed package.
11. Other objectives of this invention reside in its simplicity, aesthetics, ease of manufacture, packaging, ease of transportation, ease of use and the like which will become apparent from the following brief description of the drawings and detailed description of the preferred and alternate embodiments.

SUMMARY

The invention comprises a membrane which is reinforced at the front end of the condom with latex rubber including a cap which prevents osmotic transmission of bodily fluids.

A generic spermicide such as nonoxynol 9 is added in the latex cap as well as to the head of the condom inside of the membrane but outside of the latex which in turn deactivates HIV and like viruses of communicable diseases.

A generic spermicide is also added to the packaging to prevent drying of the membrane and to assist in the protection of some pathogens.

An elastic band is added at the front end as well as at the rear/aft end. The front end elastic is underneath the cylindrical membrane but outside of the reinforcement latex. The aft/rear end elastic is outside of the cylindrical membrane.

BRIEF DESCRIPTION OF THE DRAWING

The objectives, features and advantages of the present invention and its application will be more readily appreciated when read in conjunction with the accompanying drawing, in which.

DETAILED DESCRIPTION OF THE PREFERRED EMBODIMENT

Figure 1:
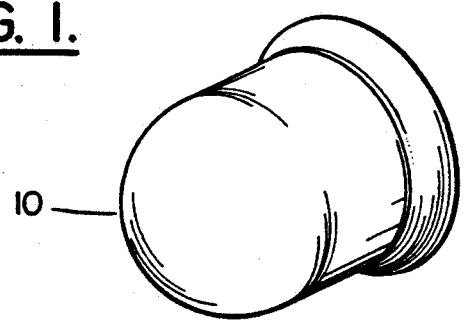
FIG. 1 is a perspective of the improved condom design of this invention in its rolled or packaged state.
Figure 2:
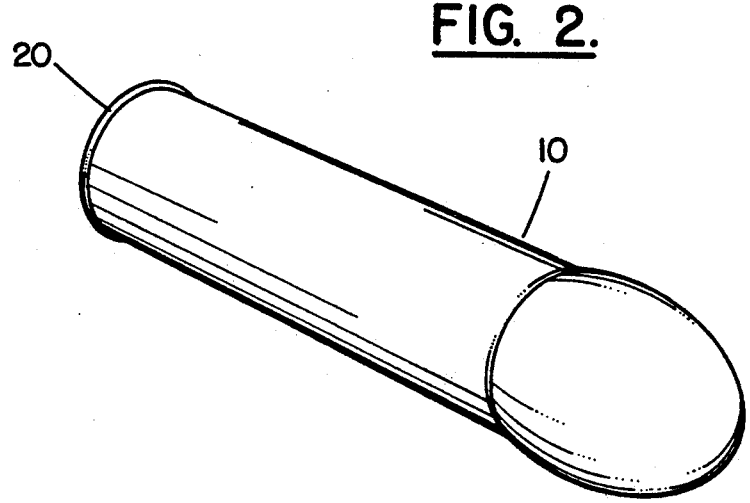
FIG. 2 is a perspective of the improved condom design of this invention as donned on a human penis.
Figure 3:
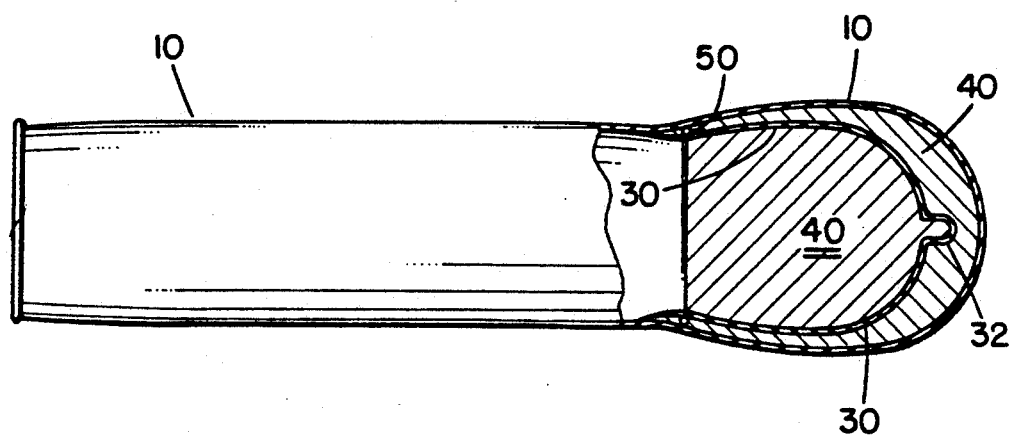
FIG. 3 is a cross sectional view of the improved condom design of this invention.

The invention comprises a cylindrical membrane 10 having circular elastic bands 20 at the rear and 50 at the front end and further which is reinforced at the head of the penis by latex rubber 30 including a cap or tip 32 which prevents osmotic transmission of bodily fluids. With this arrangement sensitivity remains at the shaft and neck of the penis while the head of the penis is protected by latex.

The latex portion of the condom including the tip 32 is attached inside the membrane portion of the head of the condom by utilizing a cement (not shown) or heat bonding technique for that attachment.

A generic spermicide 40 such as nonoxynol 9 is also added in the latex cap as well as to the head of the condom inside of the membrane but outside of the latex which in turn deactivates HIV and like viruses of communicable diseases.

This in turn prevents pregnancy in females and the spread
of all sexual diseases communicable through transmission of bodily fluids in this case sexual bodily fluids such as semen.

A generic spermicide is also added to the packaging to prevent drying of the membrane and to assist in the protection of some pathogens.

Each condom is individually wrapped as well as collectively packaged in a box. Each individually wrapped condom also has braille markings to facilitate donning of the condom even in the dark.

These condoms are however not designed to prevent spread of herpes virus or the bacterium that causes syphilis.

The inventor recommends the following steps for use of this condom.

a) Before removing the condom from the hermetically sealed package feel the braille markings to orient the condom in ready to don position.
b) Place the condom on the tip of the penis in the roll down orientation.
c) Roll down the condom.
d) Enjoy normal or improved sexual intercourse.
e) Immediately after the sexual intercourse, grasp the condom at the base of the penis with either hand and withdraw both the condom and the penis from the orifice; and
g) Grasp the condom with both hands at the base of the penis with the thumb and forefinger and pull the condom over the head of the penis until the second layer is identified, then grasp the condom with the thumb and forefinger of either hand at the head of the penis and remove condom without contaminating urethra with the membrane portion of the condom.
h) Discard the condom safely preferably in the flushable toilet.

While this condom has been described generically, it is not intended to be construed in a limiting sense. Various changes may be made to its design, construction and packaging without deviating from the spirit of this invention. Examples of such contemplated changes include but are not limited to the following.

a) A different spermicide other than that taught by this inventor may be used.
b) Condoms may be color coded by size
c) Condoms may be personalized with names, monograms, trademarks or promotional statements of the organization.
d) Different and newer materials may be used as they become available which essentially perform the same function.
e) Latex rubber or polyurethane may be attached to the inside membrane by a different method.
f) Latex rubber or polyurethane may extend through the entire length of the condom.
g) Latex rubber or polyurethane may or may not have space between the membrane.
h) Elastic bands may be positioned differently.
i) The packaging may be varied to appeal to different consumers.

Following is a listing of the components used in the preferred and alternate embodiment arranged in ascending order of the reference numerals for ready reference of the reader.

10=Cylindrical membrane
20=Elastic band at rear end of cylindrical membrane
30=Latex rubber or polyurethane reinforcement
32=cap or tip of latex rubber reinforcement
40=Spermicide such as nonoxynol 9
50=Elastic band at front end of condom underneath the membrane but outside of the latex.

While this invention has been described with reference to illustrative embodiments, this description is not intended to be construed in a limiting sense. Various modifications and combinations of the illustrative embodiments as well as other embodiments of the invention will be apparent to person skilled in the art upon reference to this description.

It is therefore contemplated that the appended claims cover any such modifications, embodiments as fall within the true scope of the invention.

The inventor claims:

1. A condom comprising:
a tubular main sheath having an open proximal end and a closed distal end;
a reinforcing membrane fixedly secured to said main sheath so as to be disposed therewithin in spaced relation to said distal end thereof and so as to define a substantially closed compartment between the reinforcing membrane and the distal end of the main sheath;
a first elastic, circular band element coupled to said main sheath at said proximal end thereof; and
a second elastic, circular band element disposed adjacent to but remote from said distal end of said main sheath, between said main sheath and said reinforcing membrane;
whereby sensitivity is preserved for the shaft and neck of the penis while the head of the penis is shielded and osmotic transmission of bodily fluids in a distal direction is prevented.

2. A condom as in claim 1, further comprising a spermicidal material disposed in said substantially closed compartment.

3. A condom as in claim 2, wherein said spermicide is nonoxynol 9.

4. A condom as in claim 1 further comprising a reservoir of spermicide disposed within said main sheath proximally of said reinforcing membrane.

5. A condom as in claim 1 in combination with and sealed within a package.

6. A condom as in claim 5, further comprising braille-like indicia projecting from an outer surface of said package whereby instructions for use of the condom can be ascertained tactilely.

7. A condom as in claim 1, wherein said reinforcing membrane comprises a latex rubber membrane.

8. A condom as in claim 1, wherein said reinforcing membrane comprises a polyurethane membrane.

9. A condom comprising:
a tubular main sheath having an open proximal end and a closed distal end;
a reinforcing membrane fixedly secured to said main sheath so as to be disposed therewithin in spaced relation to said distal end thereof and so as to define a substantially closed compartment between the reinforcing membrane and the distal end of the main sheath;
a spermicidal material disposed in said substantially closed compartment; and
an elastic band element coupled to said main sheath at said proximal end thereof;
whereby sensitivity is preserved for the shaft and neck of the penis while the head of the penis is shielded and osmotic transmission of bodily fluids in a distal direction is prevented.

* * * * *